(12) United States Patent  (10) Patent No.: US 7,558,051 B2
O'Phelan et al.  (45) Date of Patent: Jul. 7, 2009

(54) HIGH-ENERGY CAPACITORS FOR IMPLANTABLE DEFIBRILLATORS

(75) Inventors: Michael J. O'Phelan, Oakdale, MN (US); Luke J. Christenson, White Bear Lake, MN (US); James M. Poplett, Golden Valley, MN (US); Robert R. Tong, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 464 days.

(21) Appl. No.: 11/277,399

(22) Filed: Mar. 24, 2006

(65) Prior Publication Data

US 2006/0256505 A1 Nov. 16, 2006

Related U.S. Application Data

(63) Continuation of application No. 10/424,988, filed on Apr. 28, 2003, now Pat. No. 7,043,300, which is a continuation of application No. 09/165,779, filed on Oct. 2, 1998, now Pat. No. 6,556,863.

(51) Int. Cl.
*H01G 9/04* (2006.01)
(52) U.S. Cl. .................. 361/508; 361/509; 361/516; 361/523; 361/525; 361/528
(58) Field of Classification Search ................ 361/508, 361/509–512, 516–519, 523–525, 528–540; 29/25.01, 25.03

See application file for complete search history.

(56) References Cited

U.S. PATENT DOCUMENTS 3,398,333 A 8/1968 Zeppieri
(Continued)

FOREIGN PATENT DOCUMENTS

EP 0753868 1/1997
(Continued)

OTHER PUBLICATIONS

Patent Abstracts of Japan, 16 (134), Publication No. 03296207 (K. Kaname),(Dec. 26, 1991),1 p.
(Continued)

*Primary Examiner*—Nguyen T Ha
(74) *Attorney, Agent, or Firm*—Schwegman, Lundberg & Woessner, P.A.

(57) ABSTRACT

Implantable defibrillators are implanted into the chests of patients prone to suffering ventricular fibrillation, a potentially fatal heart condition. A critical component in these devices is an aluminum electrolytic capacitor, which stores and delivers life-saving bursts of electric charge to a fibrillating heart. To reduce capacitor size, manufacturers have developed special aluminum foils, such as core-etched and tunnel-etched aluminum foils. Unfortunately, core-etched foils don't work well in multiple-anode capacitors, and tunnel-etched foils are brittle and tend to break when making some common types of capacitors. Accordingly, the inventors devised a new foil structure having perforations and cavities. In an exemplary embodiment, each perforation and cavity has a cross-sectional area, with the perforations having a larger, for example, 2 to 100 times larger, average cross-sectional area than the cavities. Other embodiments of the invention include foil assemblies, capacitors, and implantable defibrillators that benefit from properties of the new foil structure.

19 Claims, 6 Drawing Sheets

U.S. PATENT DOCUMENTS

| | | |
|---|---|---|
| 3,555,369 A | 1/1971 | Yoshino et al. |
| 3,659,615 A | 5/1972 | Enger |
| 3,765,956 A | 10/1973 | Li |
| 3,789,502 A | 2/1974 | Callins et al. |
| 3,918,460 A | 11/1975 | King et al. |
| 3,943,937 A | 3/1976 | King et al. |
| 4,041,955 A | 8/1977 | Kelly et al. |
| 4,041,956 A | 8/1977 | Purdy et al. |
| 4,136,435 A | 1/1979 | Li |
| 4,183,600 A | 1/1980 | Schroeder |
| 4,243,042 A | 1/1981 | Ware |
| 4,333,469 A | 6/1982 | Jeffcoat et al. |
| 4,371,406 A | 2/1983 | Li |
| 4,385,342 A | 5/1983 | Puppolo et al. |
| 4,395,305 A | 7/1983 | Whitman |
| 4,446,188 A | 5/1984 | Patel et al. |
| 4,481,083 A | 11/1984 | Ball et al. |
| 4,521,830 A | 6/1985 | Aultman et al. |
| 4,546,415 A | 10/1985 | Kent et al. |
| 4,663,824 A | 5/1987 | Kenmochi |
| 4,676,879 A | 6/1987 | Salvadori |
| 4,690,714 A | 9/1987 | Li |
| 4,692,147 A | 9/1987 | Duggan |
| 4,771,362 A | 9/1988 | Behn |
| 4,782,235 A | 11/1988 | Lejeune et al. |
| 4,844,778 A | 7/1989 | Witte |
| 4,907,130 A | 3/1990 | Boulloy et al. |
| 4,942,501 A | 7/1990 | MacFarlane et al. |
| 4,944,300 A | 7/1990 | Saksena |
| 4,987,519 A | 1/1991 | Hutchins et al. |
| 5,055,889 A | 10/1991 | Beall |
| 5,055,975 A | 10/1991 | Behrend |
| 5,086,374 A | 2/1992 | MacFarlane et al. |
| 5,131,388 A | 7/1992 | Pless et al. |
| 5,146,391 A | 9/1992 | MacFarlane et al. |
| 5,153,820 A | 10/1992 | MacFarlane et al. |
| 5,245,499 A | 9/1993 | Senes |
| 5,275,621 A | 1/1994 | Mehra |
| 5,324,910 A | 6/1994 | Isawa |
| 5,370,663 A | 12/1994 | Lin |
| 5,380,341 A | 1/1995 | Matthews et al. |
| 5,439,760 A | 8/1995 | Howard et al. |
| 5,456,698 A | 10/1995 | Byland et al. |
| 5,468,984 A | 11/1995 | Efland et al. |
| 5,500,534 A | 3/1996 | Robinson et al. |
| 5,522,851 A | 6/1996 | Fayram |
| 5,536,960 A | 7/1996 | Hayashi |
| 5,536,964 A | 7/1996 | Green et al. |
| 5,545,184 A | 8/1996 | Dougherty |
| 5,584,890 A | 12/1996 | MacFarlane et al. |
| 5,591,211 A | 1/1997 | Meltzer |
| 5,597,658 A | 1/1997 | Kejha |
| 5,628,801 A | 5/1997 | MacFarlane et al. |
| 5,634,938 A | 6/1997 | Swanson et al. |
| 5,642,252 A | 6/1997 | Sakamoto et al. |
| 5,660,737 A | 8/1997 | Elias et al. |
| 5,661,625 A | 8/1997 | Yang |
| 5,661,629 A | 8/1997 | MacFarlane et al. |
| 5,667,909 A | 9/1997 | Rodriguez et al. |
| 5,674,260 A | 10/1997 | Weinberg |
| 5,677,539 A | 10/1997 | Apotovsky et al. |
| 5,680,685 A | 10/1997 | Bischoff |
| 5,688,698 A | 11/1997 | Robinson et al. |
| 5,697,953 A | 12/1997 | Kroll et al. |
| 5,698,453 A | 12/1997 | Green et al. |
| 5,711,861 A | 1/1998 | Ward et al. |
| 5,711,988 A | 1/1998 | Tsai et al. |
| 5,728,150 A | 3/1998 | McDonald et al. |
| 5,728,594 A | 3/1998 | Efland et al. |
| 5,748,438 A | 5/1998 | Davis et al. |
| 5,748,439 A | 5/1998 | MacFarlane et al. |
| 5,776,628 A | 7/1998 | Kraft et al. |
| 5,800,857 A | 9/1998 | Ahmad et al. |
| 5,808,857 A | 9/1998 | Stevens |
| 5,814,082 A | 9/1998 | Fayram et al. |
| 5,822,177 A | 10/1998 | Popp et al. |
| 5,837,995 A | 11/1998 | Chow et al. |
| 5,859,456 A | 1/1999 | Efland et al. |
| 5,867,363 A | 2/1999 | Tsai et al. |
| 5,895,416 A | 4/1999 | Barreras, Sr. et al. |
| 5,895,733 A | 4/1999 | Crespi et al. |
| 5,904,514 A | 5/1999 | Konuma et al. |
| 5,926,357 A | 7/1999 | Elias et al. |
| 5,930,109 A | 7/1999 | Fishler |
| 5,949,638 A | 9/1999 | Greenwood, Jr. et al. |
| 5,959,535 A | 9/1999 | Remsburg |
| 5,963,418 A | 10/1999 | Greenwood, Jr. et al. |
| 5,968,210 A | 10/1999 | Strange et al. |
| 5,980,977 A | 11/1999 | Deng et al. |
| 5,983,472 A | 11/1999 | Fayram et al. |
| 6,006,133 A | 12/1999 | Lessar et al. |
| 6,009,348 A | 12/1999 | Rorvick et al. |
| 6,110,233 A | 8/2000 | O'Phelan et al. |
| 6,141,205 A * | 10/2000 | Nutzman et al. ............ 361/509 |
| 6,249,423 B1 | 6/2001 | O'Phelan et al. |
| 6,409,776 B1 | 6/2002 | Yan et al. |
| 6,421,226 B1 * | 7/2002 | O'Phelan et al. ............ 361/509 |
| 6,426,864 B1 * | 7/2002 | O'Phelan et al. ............ 361/509 |
| 6,556,863 B1 | 4/2003 | O'Phelan et al. |
| 6,885,545 B2 * | 4/2005 | Michel et al. ............... 361/502 |
| 2004/0039421 A1 | 2/2004 | O'Phelan et al. |
| 2005/0052825 A1 | 3/2005 | O'Phelan |

FOREIGN PATENT DOCUMENTS

| | | |
|---|---|---|
| EP | 0851446 | 7/1998 |
| JP | 52-004051 | 1/1977 |
| JP | 59-083772 | 5/1984 |
| WO | WO-99/51301 | 10/1999 |
| WO | WO-99/51302 | 10/1999 |
| WO | WO-99/51303 | 10/1999 |
| WO | WO-99/66985 | 12/1999 |

OTHER PUBLICATIONS

Patent Abstracts of Japan, 18 (3), Publication No. 05251283 (T. Fumiyasu),(Sep. 28, 1993),1 p.

Patent Abstracts of Japan, 97 (12), Publication No. 09219343 (I. Toshihiko),(Aug. 19, 1997),1 p.

Patent Abstracts of Japan, 15 (40), Publication No. 02276222 (U. Noriki),(Nov. 13, 1990),1 p.

Database WPI Abstract, XP-002126511, An- 1997-031410 (03), Publication No. JP 08293430, Derwent Publications Ltd., London, GB,(Nov. 5, 1996),1 p.

Patent Abstracts of Japan, 1996 (6), Publication No. 08055762 (E. Akira),(Feb. 27, 1996),1 p.

Patent Abstracts of Japan, 16 (291), Publication No. 04074409 (A. Akiyoshi),(Jul. 16, 1990),1 p.

"Understanding Aluminum Electrolytic Capacitors", *United Chemi-Con*, (Date Unknown),7 p.

Block, Michael , "Biphasic Defibrillation Using a Single Capacitor with Large Capacitance: Reduction of Peak Voltages and ICD Device Size", *Pace*, Vo. 19, (Feb. 1996),207-214.

Block, Michael , "Internal Defibrillation with Smaller Capacitors: A Prospective Randomized Cross-Over Comparison of Defibrillation Efficacy Obtained with 90-iF and 125-iF Capacitors in Humans", *Journal of Cardiovascular Electrophysiology*, vol. 6, No. 5, (May 1995),333-342.

Brugada, J. , "Clinical evaluation of defibrillation efficacy with a new single-capacitor biphasic waveform in patients undergoing implantation of an implantable cardioverter defibrillator", *The European Society of Cardiology*, vol. 3, (Oct. 2001),278-284.

Hahn, Stephen J., et al., "Large Capacitor Defibrillation Waveform Reduces Peak Voltages Without Increasing Energies", *Pace*, vol. 18, Part II, (Jan. 1995),203-207.

Jenkins, "Diagnosis of Atrial Fibrillation Using Electrogram from Chronic Leads: Evaluation of Computer Algorithm", *Pace*, 11 (1988),pp. 622-631.

Lunsman, P., et al., "High Energy Density Capacitors for Implantable Defibrillators", *Proceedings of the 16th Capacitor and Resistor Technology Symposium*, Monteleone Hotel, New Orleans, Louisiana,(Mar. 11-15, 1996),pp. 277-280.

Morris, et al., "Intracardiac Electrogram Transformation: Morphometric Implications for Implantable Devices", *Journal of Electrocardiology*, 29 Supplement, (1996),pp. 124-129.

Moynihan, J. D., "Theory, Design and Application of Electrolytic Capacitors", Copyright by John D. Moynihan,(1982),136 p.

Schuller, et al., "Far Field R-Wave Sensing—An Old Problem Repeating", *Pace*, 19, Part II, NASPE Abstract No. 264,(1996),p. 631.

Stephany, et al., "Real-Time Estimation of Magnitude-Square Coherence for Use in Implantable Devices", *IEEE Computers in Cardiology*, (1992),pp. 375-378.

\* cited by examiner

HIGH-ENERGY CAPACITORS FOR IMPLANTABLE DEFIBRILLATORS

CROSS-REFERENCE TO RELATED APPLICATION(S)

This application is a continuation of U.S. patent application Ser. No. 10/424,988, filed on Apr. 28, 2003, now U.S. Pat. No. 7,043,300 which is a continuation of U.S. patent application Ser. No. 09/165,779, filed on Oct. 2, 1998, now issued as U.S. Pat. No. 6,556,863, the specifications of which are incorporated herein by reference.

This application is also related to U.S. patent application Ser. No. 09/606,633, filed on Jun. 29, 2000, now issued as U.S. Pat. No. 6,421,226 and U.S. patent application Ser. No. 09/606,291, filed on Jun. 29, 2000, now issued as U.S. Pat. No. 6,426,864, the specifications of which are incorporated herein by reference.

BACKGROUND OF THE INVENTION

The present invention concerns electrolytic capacitors, particularly those for use in medical devices, such as implantable defibrillators.

Every year more than half a million people in the United States suffer from heart attacks, more precisely cardiac arrests. Many of these cardiac arrests stem from the heart chaotically twitching, or fibrillating, and thus failing to rhythmically expand and contract as necessary to pump blood. Fibrillation can cause complete loss of cardiac function and death within minutes. To restore normal heart contraction and expansion, paramedics and other medical workers use a device, called a defibrillator, to electrically shock a fibrillating heart.

Since the early 1980s, thousands of patients prone to fibrillation episodes have had miniature defibrillators implanted in their bodies, typically in the left breast region above the heart. These implantable defibrillators detect onset of fibrillation and automatically shock the heart, restoring normal heart function without human intervention. A typical implantable defibrillator includes a set of electrical leads, which extend from a sealed housing into the heart of a patient after implantation. Within the housing are a battery for supplying power, heart-monitoring circuitry for detecting fibrillation, and a capacitor for storing and delivering a burst of electric charge through the leads to the heart.

The capacitor is typically an aluminum electrolytic capacitor, which usually includes a sandwich-like assembly of two strips of aluminum foil with two strips of paper, known as separators, between them. One of the aluminum foils serves as a cathode (negative) foil, and the other serves as an anode (positive) foil. Sometimes, two foils are stacked one on the other to form a dual anode. Attached to each foil is an aluminum tab which electrically connects the foil to other parts of the capacitor.

The foil-and-paper assembly, known as an active element, is then placed in a case, usually made of aluminum, and the paper is soaked, or impregnated, with a liquid electrolyte—a very electrically conductive solution containing free positive or negative ions. After the paper is impregnated, the case is sealed shut with a lid called a header. Extending from the header are two terminals connected respectively to the anode foil and cathode foil via the aluminum tabs.

In recent years, manufacturers of aluminum electrolytic capacitors have improved capacitor performance through the development of aluminum foils with increased surface areas. Increasing surface area of a foil, particularly the anode foil, increases capacitance and thus the charge-storage capacity of a capacitor.

One approach to increasing surface area of a foil is to chemically etch microscopic hills and valleys into both sides of the foil. The etching depth is controlled to leave a solid core layer between the sides of the foil. Thus, foils with this type of etching are called "core etched." Although core-etched foils have more surface area, they don't work as well as expected in capacitors with two stacked anode foils, because the solid core layer of one anode foil shields the other anode foil from electrolyte flow.

Another approach, known as tunnel etching, entails etching both sides of a foil to form millions of tiny holes, or tunnels, completely through the foil, from one side to the other. The tunnels, which typically have an approximately circular cross-section about one-micron in diameter, allows electrolyte to flow through the foil. Thus, tunnel-etched foils overcome the electrolyte-flow problem of core-etched foils.

However, tunnel-etched foils not only have less surface area than core-etched foils but are also quite brittle and tend to break easily, particularly when rolling or winding the foils to form cylindrical capacitors. Accordingly, there remains a need to develop more durable foil structures.

SUMMARY OF THE INVENTION

To address these and other needs, the present inventors devised a new foil structure which combines the durability of core-etched foils with the electrolyte-flow advantages of tunnel-etched foils. In addition to devising methods for making the new foil structure, the inventors applied the new foil structure in novel ways to build new capacitor foil assemblies and new capacitors in cylindrical and flat configurations, for example. Ultimately, these advances allow construction of smaller medical devices, such as implantable defibrillators.

Specifically, one embodiment of the new foil structure is a foil having one or more holes or perforations and one or more cavities with a depth less than the foil thickness. In an exemplary embodiment, each perforation and cavity has a cross-sectional area, with the perforations having a larger, for example, 2 to 100 times larger, average cross-sectional area than the cavities. One method of making the new foil structure includes perforating a foil and forming cavities into one or both of its surfaces. Other methods form the cavities before perforating the foil.

DETAILED DESCRIPTION

The following detailed description, which references and incorporates FIGS. 1-7, describes and illustrates one or more exemplary embodiments of the invention, specifically a new foil structure and method of manufacture, several new foil assemblies, new capacitors incorporating the foil structure and foil assemblies, and an implantable defibrillator incorporating one or more of the new capacitors. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

Exemplary Foil Structure and Methods of Manufacture

Figure 1:
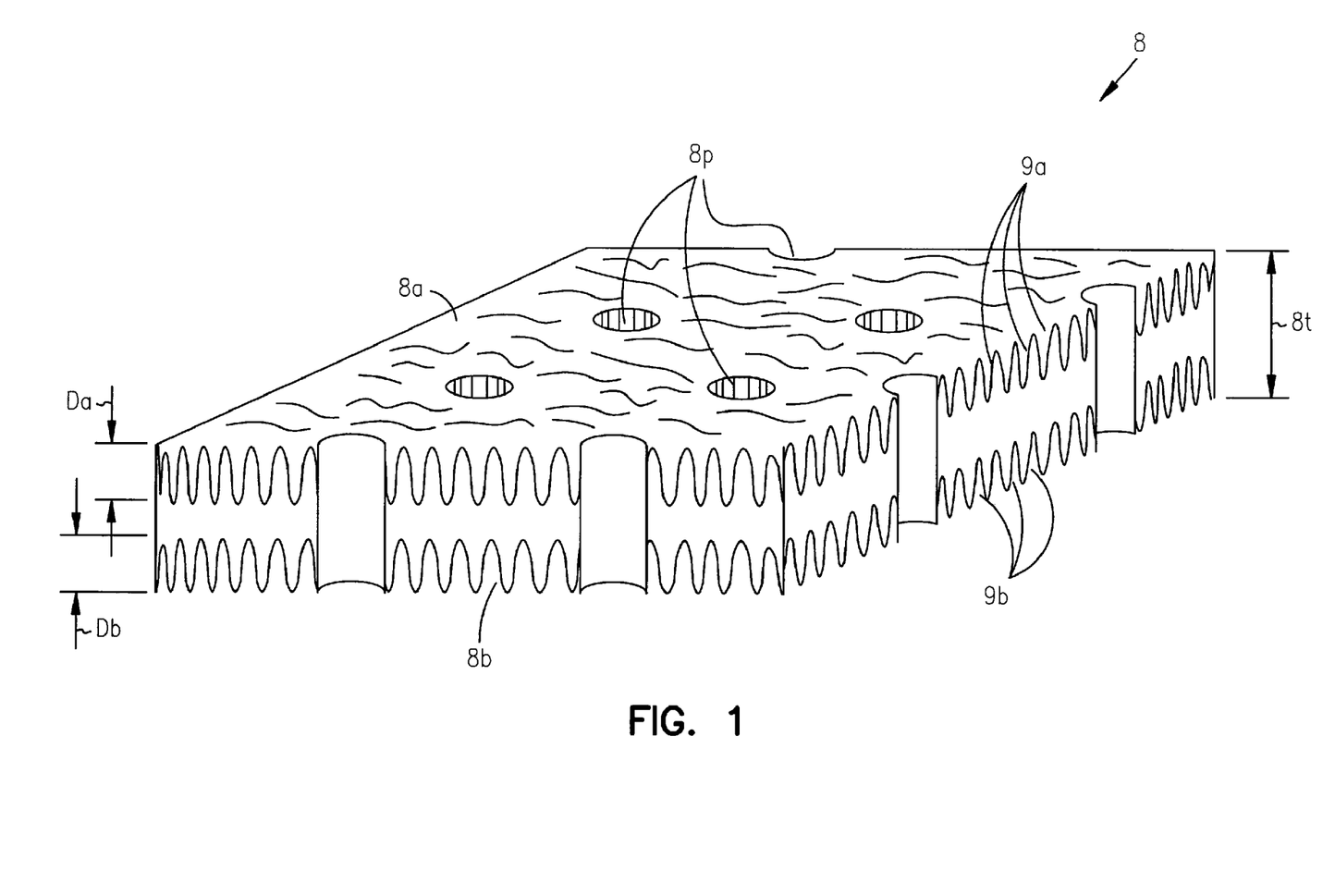
FIG. 1 is an enlarged perspective view of an exemplary foil structure 8 that embodies the invention.

FIG. 1 shows an enlarged perspective view of a foil structure 8 which the inventors call a "perforated-core-etched" foil. Foil structure 8 can be made of aluminum, tantalum, hafnium, niobium, titanium, zirconium, and combinations of these metals. However, the invention is not limited to any particular foil composition or class of foil compositions.

Foil structure 8 includes opposing surfaces 8a and 8b which define an average foil thickness 8t and a set of perforations 8p which extend through foil structure 8 from surface 8a to surface 8b. Surfaces 8a and 8b include respective sets of surface cavities (or depressions) 9a and 9b, which have generally cylindrical, conical, or hemispherical shapes. However, the invention is not limited to any particular cavity form, class of cavity forms, or combination of cavity forms. Surface cavities 9a have an average maximum depth Da which is less than thickness 8t, and surface cavities 9b having an average maximum depth Db which is also less than thickness 8t. As FIG. 1 shows, depths Da and Db are measured along dimensions generally perpendicular to respective surfaces 8a and 8b. Cavities 9a and 9b also have respective average maximum cross-sectional areas Sa and Sb (which are not shown in the figure.) Cross-sectional area is measured in a plane substantially parallel to one of surfaces 8a and 8b.

In the exemplary embodiment, average maximum depths Da and depths Db are approximately equal to one third or one quarter of thickness 8t, and cross-sectional areas Sa and Sb are substantially equal and range inclusively between about 0.16 and 0.36 square-microns. However, other embodiments use different equal and unequal depths Da and Db and different and unequal cross-sectional areas Sa and Sb.

More generally, the exemplary embodiment adheres to the constraint that the sum of average maximum depths Da and Db is less than thickness 8t. Adherence to this constraint ensures that a significant number of cavities 9a are separated from a significant number of cavities 9b by a solid region of foil material. These regions of solid material not only provide foil structure 8 with greater structural integrity but also greater surface area than conventional tunnel-etched foils. However, in some embodiments of the invention, one or more of cavities 9a intersect one or more of cavities 9b, thereby forming openings through the foil. The number of these intersections and resultant openings can be regulated through selection of appropriate cavity formation techniques and cavity depths.

In addition to surface cavities 9a and 9b, FIG. 1 shows that foil structure 8 includes a set of one or more perforations (or holes) 8p. Perforations 8p have an average maximum cross-sectional area Sp measured in a plane substantially parallel to one of surfaces 8a and 8b. Although perforations 8p have a generally circular cross-section in the exemplary embodiment, other embodiments use perforations with elliptical, triangular, square, or rectangular cross-sections. Thus, the invention is not limited to any particular shape or class of shapes. The layout or arrangement of perforations 8p takes any number of forms, including for example, a random distribution and a specific pattern with each perforation having a predetermined position relative to other perforations. The number of perforations per unit area is chosen to optimize relevant criteria, such as capacitor electrical performance or foil structural properties.

In the exemplary embodiment, average maximum cross-sectional area Sp of perforations 8p is larger than average maximum cross-sectional areas Sa and Sb of cavities 9a and 9b. More precisely, area Sp in the exemplary embodiment ranges between about 500 square-microns and 32 square-millimeters. In other embodiments, area Sp ranges between 2-50, 10-75, 25-100, or 2-100 times larger than surface areas Sa and Sb. Additionally, the exemplary embodiment provides a total perforation area (number of perforations times average maximum cross-sectional area Sp) which is no more than about 20 percent of the foil surface area.

The inventors have devised a number of ways of making foil structure 8. For example, one method initially core-etches a foil using conventional etching techniques to form cavities 9a and 9b and then perforates the core-etched foil. Another method entails initially perforating a foil to form perforations 8p and then etching the perforated foil to form cavities 9a and 9b. (For more details on a conventional etching technology, see, for example, U.S. Pat. No. 4,395,305 to Whitman, which is entitled Chemical Etching of Aluminum Capacitor Foil and incorporated herein by reference.) Perforations 8p can be formed using lasers, chemical etchants, or mechanical dies, for example. Conceptually, cavities 9a and 9b could also be formed using lasers. Thus, the invention is not limited to any particular technique or combination of techniques for forming perforations 8p and cavities 9a and 9b.

In one embodiment of the invention, further processing of the foils, particularly those intended for electrolytic capacitors, entails applying an insulative, or dielectric, coating to one or both sides of the foils. Examples of suitable coatings include metallic oxides such as aluminum or tantalum oxide.

Exemplary Foil Assemblies Incorporating the New Foil Structure

Foil structure 8 can be combined with other foils structures to form various electrically and/or mechanically advantageous foil assemblies. Many of these assemblies are particularly useful as multiple anodes structures in flat, semi-cylindrical, and cylindrical capacitors.

In particular, the inventors devised several foil assemblies that combine foil structure 8 with core-etched and tunnel-etched foils. For example, one foil assembly stacks two or three foils incorporating foil structure 8 to form a dual- or triple-foil assembly which can serve as a dual or triple anode. Another foil assembly stacks a core-etched foil between two foils incorporating foil structure 8. Table 1 describes these and several other foil assemblies.

TABLE 1

| Foil Assembly No. | Structure |
|---|---|
| 1 | PP |
| 2 | PPP |
| 3 | PCP |
| 4 | PPCPP |
| 5 | PTP |
| 6 | PTPT |
| 7 | TPT |
| 8 | PTCTP |

In the table, P denotes a perforated foil similar to foil structure 8; C denotes a core-etched foil; and T denotes a tunnel-etched foil. Thus, for example, foil assembly 7 comprises a foil similar to foil structure 8 between two tunnel-etched foils. Other novel assemblies result from combining two or more of these assemblies. For instance, combining two assembly 1s yields a PPPP structure, and combining assemblies 2 and 3 yields a PPPPCP structure. Additionally, still other novel assemblies result from inserting insulators and electrolyte-impregnated substrates, such as paper, between adjacent foils of an assembly.

Exemplary Capacitor Incorporating the New Foil Structure

Figure 2:
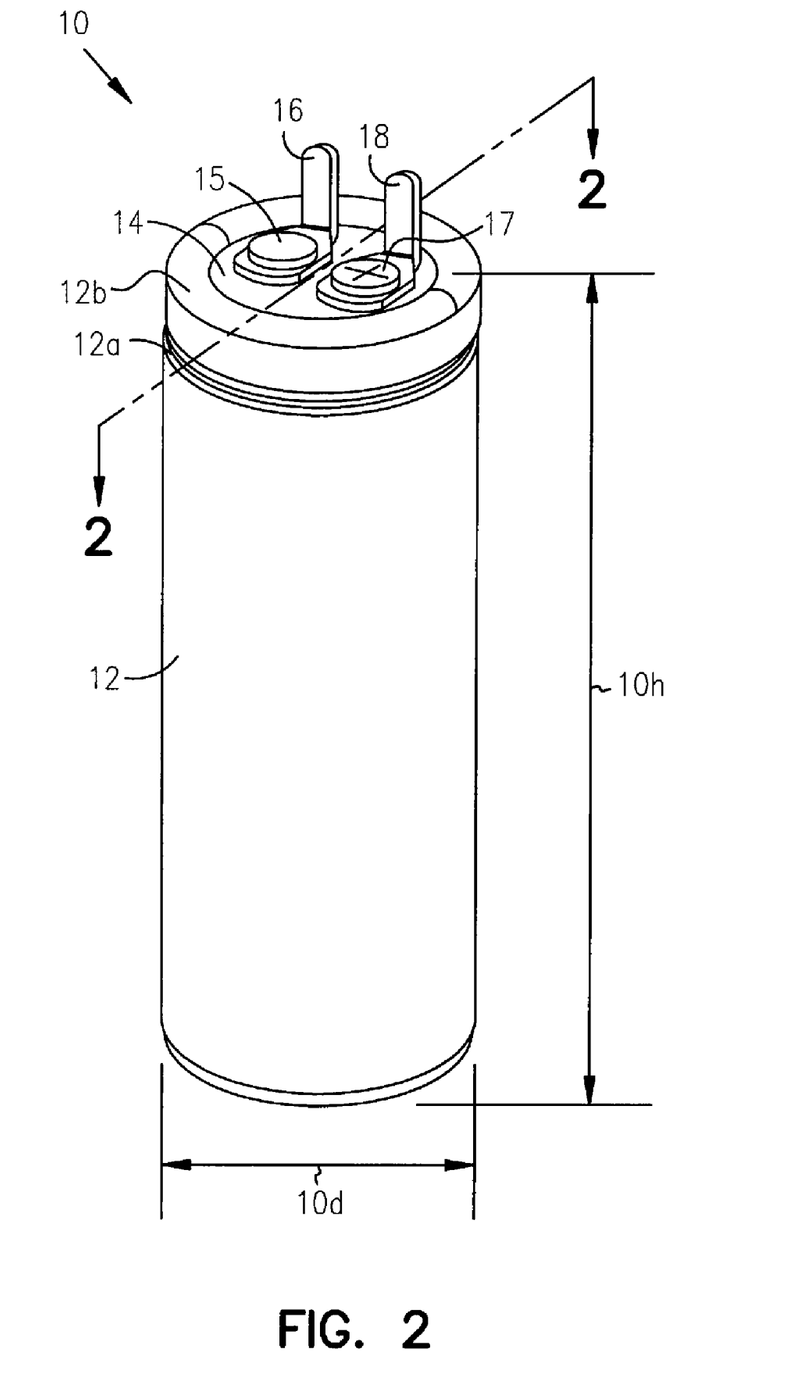
FIG. 2 is a perspective view of an exemplary cylindrical electrolytic capacitor 10 which incorporates the foil structure of FIG. 1.

FIG. 2 shows a perspective view of an exemplary electrolytic capacitor 10 which incorporates one or more foils incorporating foil structure 8 or one or more of the foil assemblies described above. In addition to incorporating these novel foils and foil assemblies, capacitor 10 embodies many novel space-saving features. These features and their advantages are addressed in a co-pending U.S. patent application Ser. No. 09/163,728 which is entitled Smaller Electrolytic Capacitors for Implantable Defibrillator, and which was filed on the same day as the present application. This application is incorporated herein by reference.

More specifically, FIG. 2 shows that capacitor 10 has a diameter 10*d* of about 14.5 millimeters and a total height 10*h* of about 30 millimeters, thereby occupying a total volume of about five cubic-centimeters. Capacitor 10 also includes a cylindrical aluminum case 12, a header (or lid) 14, and two aluminum terminals 16 and 18. Two rivets 15 and 17 fasten terminals 16 and 18 to header 14. Case 12, which houses an active element 20 (not visible in this view), includes a circumferential seating groove 12*a* and a rolled lip 12*b*, both of which secure header 14 to case 12.

Figure 3:
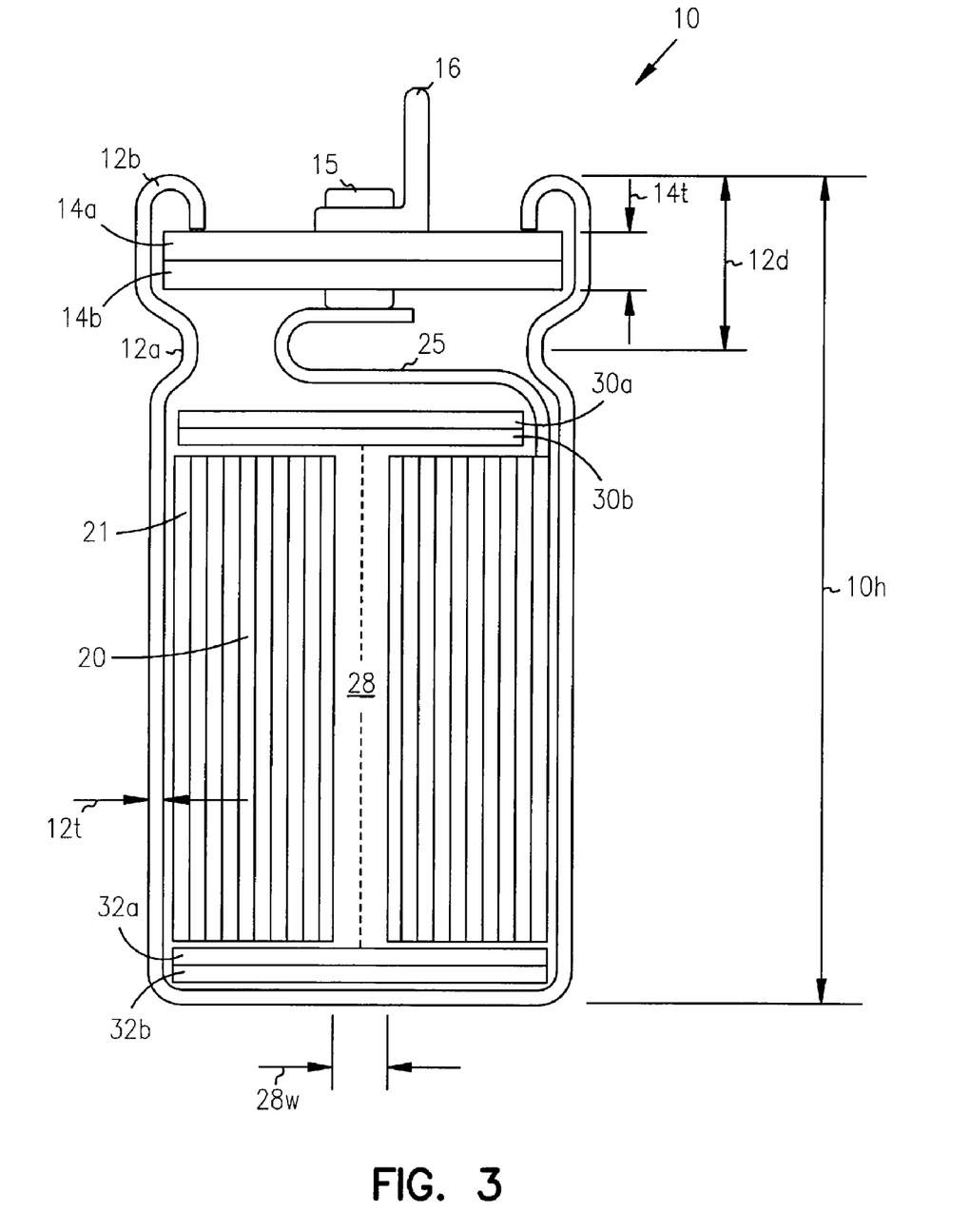
FIG. 3 is a cross-sectional view of an exemplary electrolytic capacitor 10 which incorporates the foil structure of FIG. 1.

FIG. 3, a cross-sectional view taken along line 3-3 in FIG. 2, shows that case 12 has a thickness 12*t* and groove 12*a* is spaced a distance 12*d* from lip 12*b*. Thickness 12*t* is about 0.010 inches, and distance 12*d* is about 0.145 inches. Additionally, groove 12*a* has a radius of about 0.035 inches, and lip 12*b*, which is formed by rolling over the top edge of case 12, has a radius of about 0.015 inches. (Some embodiments compress or flatten groove 12*a* to reduce capacitor height and volume.) Header 14, which comprises a rubber layer 14*a* and a phenolic-resin layer 14*b*, has a total thickness 14*t* of about two millimeters.

FIG. 3 also shows that capacitor 10 includes an active element 20 wound around mandrel region 28 and two pairs of insulative inserts 30*a*-30*b* and 32*a*-32*b* respectively positioned adjacent the top and bottom of active element 20. Mandrel region 28 has an exemplary width or diameter 28*w* of about 2.5 millimeters. And, insulative inserts 30*a*-30*b* and 32*a*-32*b* comprise respective pairs of paper disks, with each disk having a thickness of one one-thousandth of an inch and a diameter of about 14 millimeters The insulative inserts ensure electrical isolation of conductive portions of active element 20 from anode tab 25 and rivets 15 and 17 and from the bottom interior surface of case 12. (As an alternative to insulative inserts, other embodiments enclose substantially all of active element 20 within an insulative bag.) For clarity, FIG. 3 omits a 1.125-inch-wide plastic insulative sheath that surrounds the vertical surfaces of active element 20.

Figure 4:
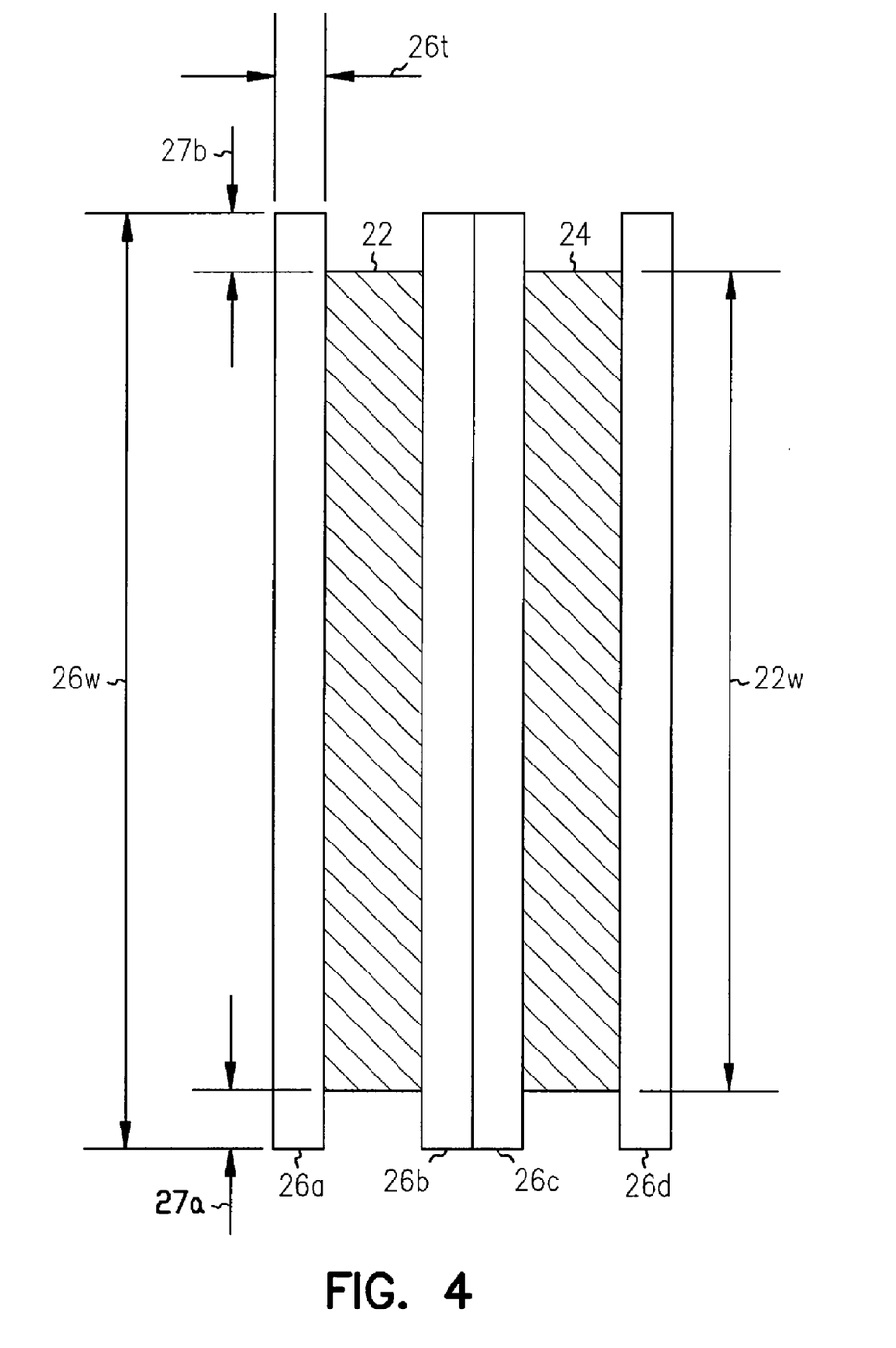
FIG. 4 is a cross-sectional view of a layered capacitive assembly 21 which forms an active element 20 of capacitor 10 and which incorporates the FIG. 1 foil structure.

Active element 20 comprises about 19 turns of a layered capacitive assembly 21. As the cross-section in FIG. 4 shows, capacitive assembly 21 includes a cathode 22, an anode structure 24, and four electrolyte-impregnated separators 26*a*, 26*b*, 26*c*, and 26*d*. Cathode 22 and anode 24 each have a width (or height) 22*w*. In this exemplary embodiment, cathode 22 and the one or more constituents of anode structure 24 are about 24 millimeters wide and 100 microns thick. Cathode 22 is about 422 millimeters long, and anode structure 24 is about 410 millimeters long.

Anode structure 24 can assume a variety of novel forms, the simplest being a single foil member incorporating foil structure 8 of FIG. 1. Some embodiments provide anode structure 24 with one or more of the novel foil assemblies described using Table 1.

Although not shown in FIG. 4, the exemplary embodiment connects anode structure 24 to one anode tab regardless of the number of foils constituting the anode structure. (FIG. 3 shows an exemplary aluminum anode tab 25.) Other embodiments, however, provide individual anode tabs for each anode members, with the tabs connected together to form a joint or composite anode tab. For more details on these or other types of tabs incorporated in other embodiments of the invention, see co-pending U.S. Pat. Nos. 6,249,423 and 6,110,233 which are respectively entitled Electrolytic Capacitor and Multi-Anodic Attachment and Wound Multi-Anode Electrolytic Capacitor with Offset Anodes and which are incorporated herein by reference.

Anode tab 25, shown in FIG. 3, is ultrasonically welded to rivet 15 and thus electrically connected to terminal 16. The exemplary embodiment folds anode tab 25 over itself; however, other embodiments omit this fold to reduce the space between header 14 and the top of active element 20. Though not visible in FIG. 3 or 4, cathode 22 includes a cathode tab which is similarly connected via rivet 17 to terminal 18.

In addition to cathode 22 and anode 24, FIG. 4 shows that capacitive assembly 21 includes thin electrolyte-impregnated separators 26, specifically 26*a*, 26*b*, 26*c*, and 26*d*. In the exemplary embodiment, separators 26*a*-26*d* each consists of kraft paper impregnated with an electrolyte, such as an ethylene-glycol base combined with polyphosphates or ammonium pentaborate, and each has a thickness less than 0.001 inches. More specifically, the exemplary embodiment uses one or more papers of the following thicknesses: 0.000787, 0.0005 inches, and 0.00025 inches, with thicker papers preferably placed nearer the center of the active element to withstand the greater tensile stress that interior separators experience during winding.

Additionally, each of separators 26*a*-26*d* has a width 26*w* which is less than four millimeters wider than cathode 22 and anode 24 to provide end margins 27*a* and 27*b*. In the exemplary embodiment, width 26*w* is about 27 millimeters, or three millimeters wider than cathode 22 and anode 24, to provide end margins 27*a* and 27*b* of about 1.5 millimeters. Other embodiments of the invention provide at least one end margins of about 1.75, 1.25, 1, 0.75, 0.5, 0.25, and even 0.0 millimeters.

Figure 5A:
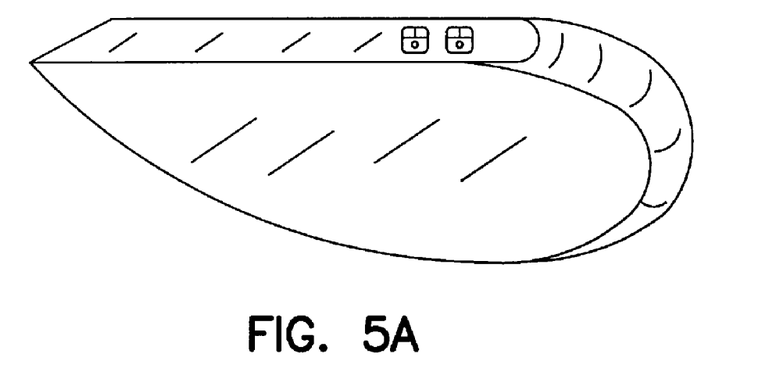
FIGS. 5A-5C are perspective views of other capacitor configurations that incorporate the FIG. 1 foil structure.
Figure 5B:
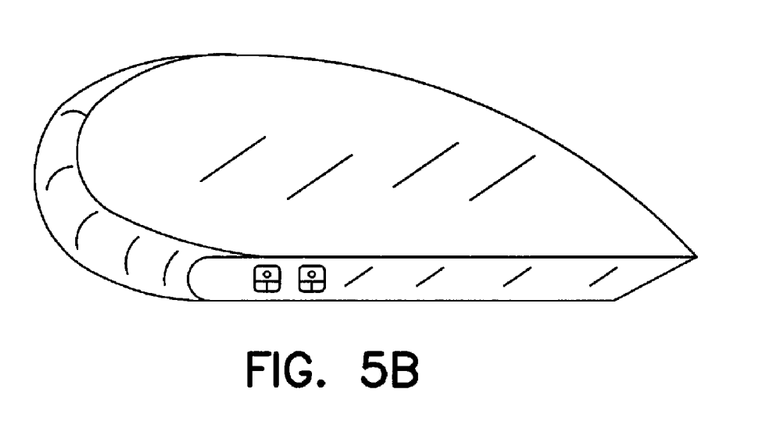
Figure 5C:
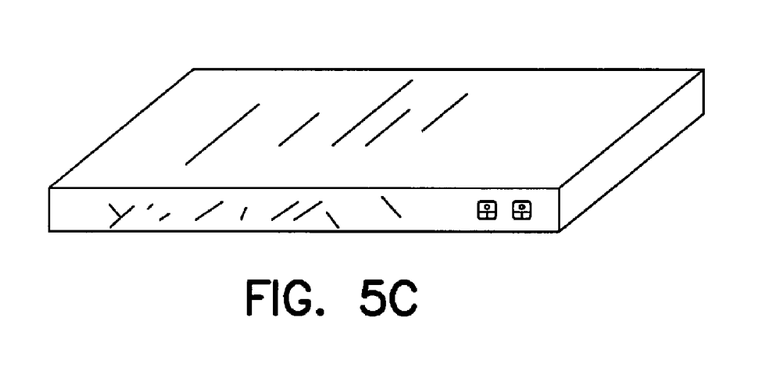
Figure 6:
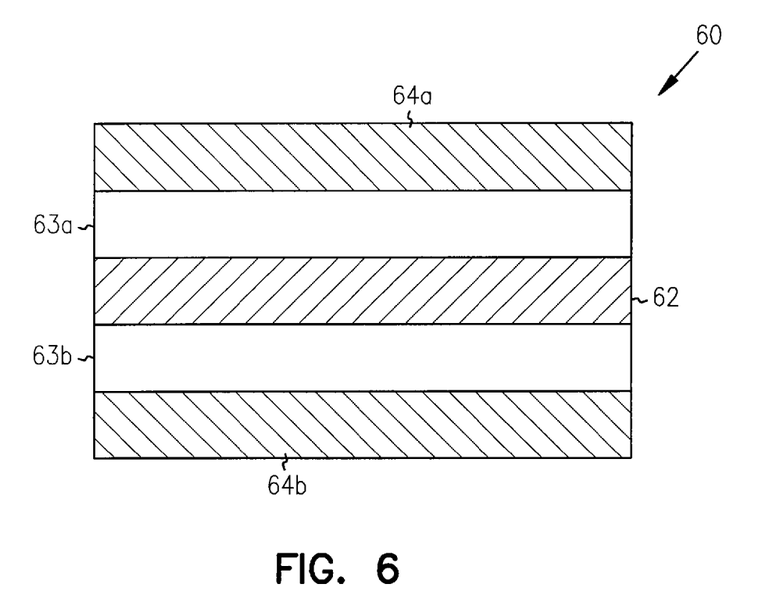
FIG. 6 is a cross-sectional view of a symmetric capacitive assembly 60 which incorporates the FIG. 1 foil structure and which is particularly suited for flat capacitor configurations.

Although the exemplary capacitor 10 has a wound or cylindrical configuration, the invention is not limited to any particular type or category of configurations. For example, FIGS. 5A, 5B, and 5C show other capacitor configurations encompassed by the invention. More specifically, FIG. 5A shows a semi-cylindrical (or "D") capacitor; FIG. 5B shows an asymmetric semi-cylindrical capacitor; and FIG. 5C shows a flat (or more precisely a rectangular parallelepiped) capacitor. FIG. 6 show a cross-sectional view of a capacitive assembly 60 particularly useful for flat capacitors such as the one shown in FIG. 5C.

In particular, capacitive assembly 60 includes an anode structure 62 between two cathode foils 64a and 64b. Electrolyte-impregnated separators 63a and 63b lie respectively between anode structure 62 and cathode foils 64a and 64b. In the exemplary embodiment separators 63a and 63b each comprise two or more layers of kraft paper of thicknesses similar to separators 26 of FIG. 4. Anode structure 62 comprises one or more of the foil assemblies identified in Table 1.

Exemplary Embodiment of Implantable Defibrillator

Figure 7:
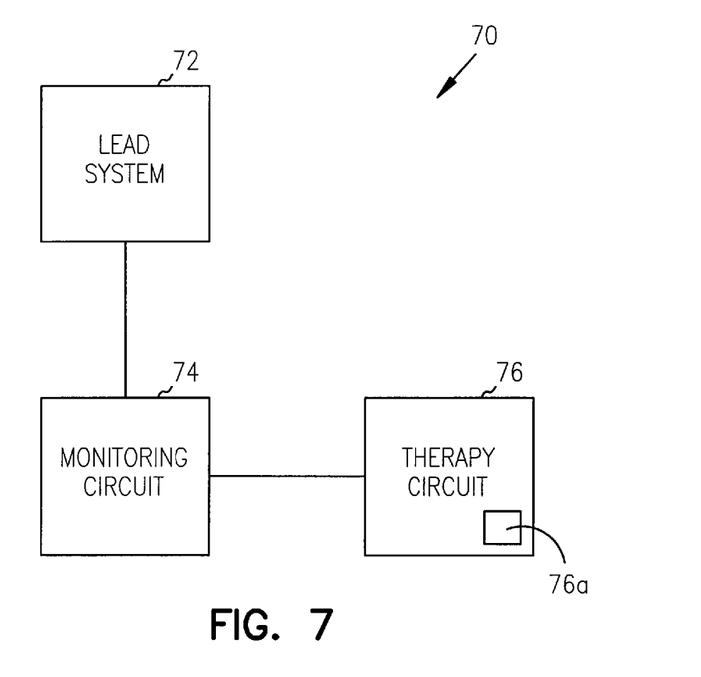
FIG. 7 is a block diagram of generic implantable defibrillator 70 including a capacitor that incorporates the FIG. 1 foil structure.

FIG. 7 shows one of the many applications for exemplary capacitor 10: a generic implantable defibrillator 70. More specifically, defibrillator 70 includes a lead system 72, which after implantation electrically contacts strategic portions of a patient's heart, a monitoring circuit 74 for monitoring heart activity through one or more of the leads of lead system 72, and a therapy circuit 76 which delivers electrical energy through lead system 72 to the patient's heart. Therapy circuit 76 includes an energy storage component 76a which incorporates at least one capacitor having one or more of the novel features of capacitor 10. Defibrillator 70 operates according to well known and understood principles.

In addition to implantable defibrillators, the innovations of capacitor 10 can be incorporated into other cardiac rhythm management systems, such as heart pacers, combination pacer-defibrillators, and drug-delivery devices for diagnosing or treating cardiac arrhythmias. They can be incorporated also into non-medical applications, for example, photographic flash equipment. Indeed, the innovations of capacitor 10 are pertinent to any application where small, high energy, low equivalent-series-resistance (ERS) capacitors are desirable.

Conclusion

In furtherance of the art, the inventors devised a new foil structure which combines the durability of core-etched foils with the electrolyte flow advantages of tunnel-etched foils. In addition to devising methods for making the new foil structure, the inventors applied the new foil structure to build new capacitors and implantable defibrillators.

The embodiments described above are intended only to illustrate and teach one or more ways of practicing or implementing the present invention, not to restrict its breadth or scope. The actual scope of the invention, which embraces all ways of practicing or implementing the concepts and principles of the invention, is defined only by the following claims and their equivalents.

What is claimed is:

1. A capacitor comprising a foil having a foil thickness; means, including at least eight perforations, for allowing passage of an electrolyte; and one or more cavities having a depth less than the foil thickness.

2. The capacitor of claim 1, wherein the foil has first and second opposing sides, with one or more of the cavities on the first side and one or more of the cavities on the second side and wherein the average depth of the cavities is less than one-half the foil thickness.

3. The capacitor of claim 2, wherein the average depth of the cavities is about one-third or one-fourth of the foil thickness.

4. The capacitor of claim 1, wherein the perforations have an average cross-sectional area larger than an average cross-sectional area of the cavities.

5. The capacitor of claim 1, wherein each perforation has a generally circular shape.

6. The capacitor of claim 1, wherein the foil comprises at least one of aluminum, tantalum, hafnium, niobium, titanium, and zirconium.

7. The capacitor of claim 1, wherein at least a portion of the foil is rolled.

8. A capacitor comprising:
a foil having first and second opposing surfaces which define a foil thickness, with the first opposing surface having one or more cavities each having a maximum depth less than the foil thickness and the second opposing surface having one or more cavities each having a maximum depth less than the foil thickness; and
means, including at least six perforations, for allowing passage of electrolyte through the foil.

9. The capacitor of claim 8:
wherein the cavities of the first surface have a first average depth and the cavities of the second surface have a second average depth, with the first and second average depths being less than one-half the foil thickness; or
wherein the perforations have an average cross-sectional area at least twice an average maximum cross-sectional area of the cavities; or
wherein at least a portion of the foil is rolled.

10. The capacitor of claim 8, wherein the foil comprises at least one of aluminum, and titanium.

11. The capacitor of claim 8, wherein each perforation has a generally circular shape.

12. An aluminum electrolytic capacitor comprising:
at least one aluminum anode foil having first and second opposing surfaces which define a foil thickness, with the first opposing surface having one or more cavities and the second opposing surface having one or more cavities, the cavities of the first and second surfaces having an average maximum depth less than one half the foil thickness and having an average maximum cross-sectional area; and
means, including at least six perforations, for allowing passage of electrolyte through the aluminum anode foil, with the perforations having an average maximum cross-sectional area at least twice the average maximum cross-sectional area of the cavities.

13. The aluminum electrolytic capacitor of claim 12:
wherein the average depth of the cavities is about one-third or one-fourth the foil thickness; or
wherein the perforations have an average maximum cross-sectional area about 2 to 100 times larger than the average maximum cross-sectional area of the cavities.

14. The capacitor of claim 13, wherein the foil comprises titanium.

15. The capacitor of claim 13, wherein each perforation has a generally circular shape.

16. A capacitor comprising:
at least one perforated-core-etched foil; or
at least one perforated-core-etched foil adjacent at least one core-etched foil; or at least one perforated-core-etched foil, at least one core-etched foil, and at least one tunnel-etched foil;

wherein each perforated core-etched foil comprises:

first and second opposing surfaces which define a foil thickness, with the first opposing surface having one or more cavities each having a maximum depth less than the foil thickness and the second opposing surface having one or more cavities each having a maximum depth less than the foil thickness: and means, including at least six perforations, for allowing passage of electrolyte through the foil.

17. The capacitor of claim 16 wherein the cavities of the first surface have a first average depth and the cavities of the second surface have a second average depth, with the first and second average depths being less than one-half the foil thickness.

18. The capacitor of claim 16, wherein the foil comprises titanium.

19. The capacitor of claim 16, wherein each perforation has a generally circular shape.

* * * * *